United States Patent [19]

Floyd, Jr.

[11] 4,021,452
[45] May 3, 1977

[54] 2,5-DIHYDRO-2,5-DIALKOXYFURAN DERIVATIVES

[75] Inventor: Middleton Brawner Floyd, Jr., Suffern, N.Y.

[73] Assignee: American Cyanamid Company, Stamford, Conn.

[22] Filed: Jan. 29, 1976

[21] Appl. No.: 653,671

Related U.S. Application Data

[62] Division of Ser. No. 571,041, April 23, 1975, Pat. No. 3,952,033.

[52] U.S. Cl. .................. 260/347.3; 260/347.5; 260/347.8
[51] Int. Cl.² ............................. C07D 307/32
[58] Field of Search .......... 260/347.3, 347.5, 347.8

[56] References Cited

FOREIGN PATENTS OR APPLICATIONS 2,176,845  11/1973   France

OTHER PUBLICATIONS

Novitskii et al., Chem. Ab. vol. 78, (1973) 71807.
Novitskii et al. Chem. Ab. vol. 77, (1972) 48368.

*Primary Examiner* — Henry R. Jiles
*Assistant Examiner* — Bernard Dentz
*Attorney, Agent, or Firm* — Denis A. Polyn

[57] ABSTRACT

This disclosure describes novel 2,5-dihydro-2,5-dialkoxyfuran derivatives useful as intermediates for the preparation of the natural prostaglandins and their congeners.

5 Claims, No Drawings

2,5-DIHYDRO-2,5-DIALKOXYFURAN DERIVATIVES

This a division of application Ser. No. 571,041, filed Apr. 23, 1975, now U.S. Pat. No. 3,952,033.

BRIEF SUMMARY OF THE INVENTION

This invention relates to novel compounds useful as intermediates for the synthesis of the natural prostaglandins and their congeners. These novel compounds may be represented by the following structural formula:

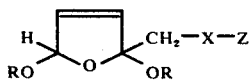

wherein R is a lower alkyl group of 1 to 4 carbon atoms; X is a divalent alkylene group of from 1 to 9 carbon atoms optionally substituted with one or two lower alkyl groups of from 1 to 4 carbon atoms, or a divalent alkylene group of from 3 to 9 carbon atoms having one double bond and optionally substituted with one or two lower alkyl groups of from 1 to 4 carbon atoms; and Z is a formyl, carboxy or carboalkoxy group wherein the alkoxy moiety has from 1 to 12 carbon atoms. The invention also relates to compounds of the formula:

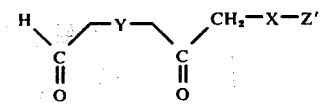

wherein X is as defined hereinabove; Z′ is a carboxy or carboalkoxy group wherein the alkoxy moiety has from 1 to 12 carbon atoms; and Y is ethylene or cis-vinylene.

DETAILED DESCRIPTION OF THE INVENTION

The formation of the novel compounds of this invention and their ultimate conversion to prostaglandins may be accomplished as illustrated in the following Flowsheet for the synthesis of prostaglandins $E_2$ (XII) and $E_1$ (XXII), and 11-deoxyprostaglandins $E_2$ (XIV) and $E_1$ (XXVI). In the Flowsheet, R is as defined hereinabove.

FLOWSHEET

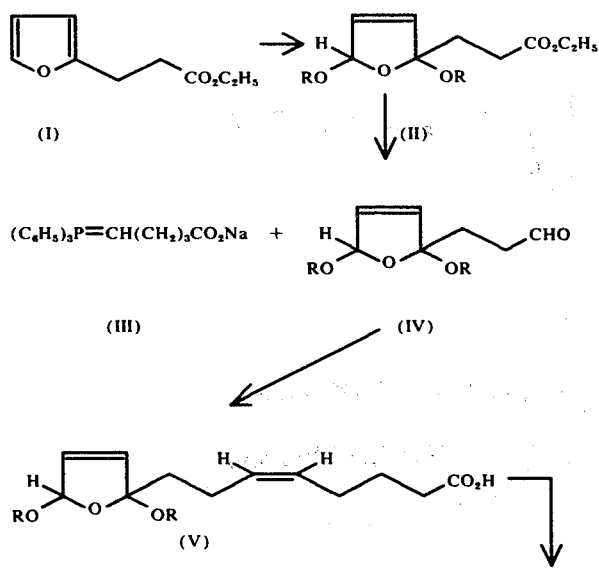

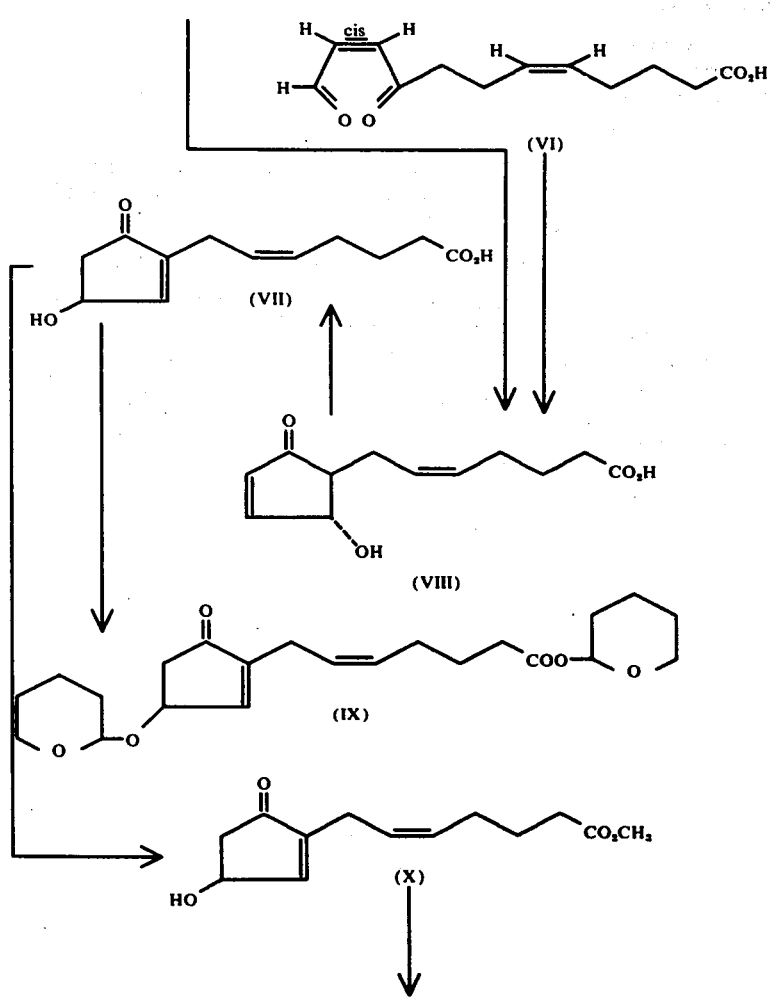
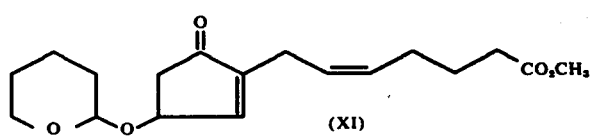
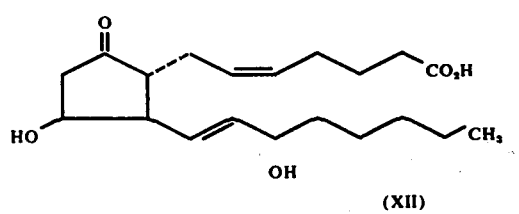

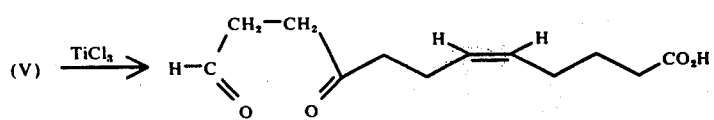
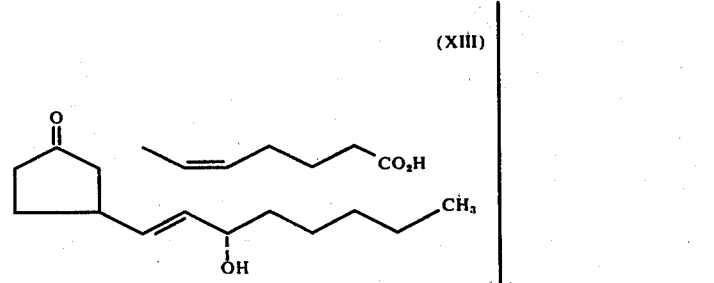
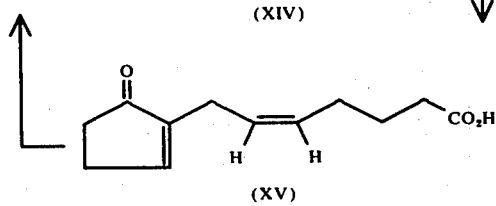
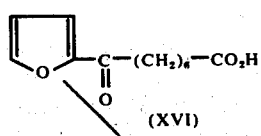
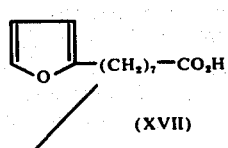
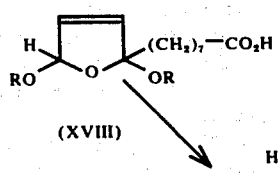
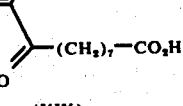
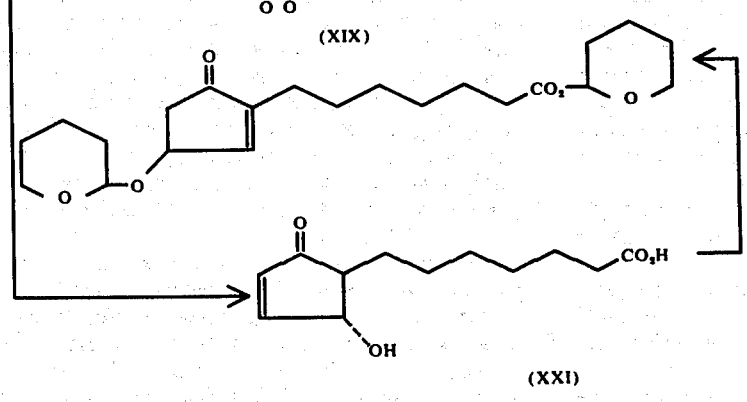

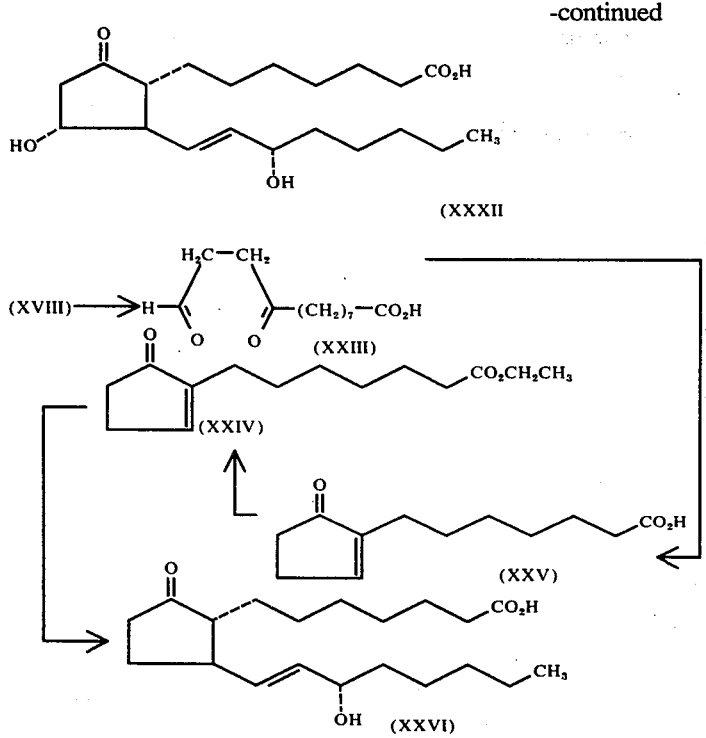

In accordance with the illustrative equations of the Flowsheet hereinabove, ethyl α-(2-furyl)propionate (I) [I. F. Bel'skii, et al., *Dokl. Akad. Nauk SSSR*, 152, 862 (1963); *Chem. Abstr.*, 60, 1577d (1964)] is subjected to oxidative alkoxylation, for example with bromine in a lower alkonal (e.g. methanol) in the presence of a base such as sodium carbonate or sodium acetate [N. Clauson-Kaas, *Acta. Chem. Scand.*, 1, 619 (1947)] or by electrolysis [N. Clauson-Kaas et al. ibid., 6, 531 (1952)] to provide the ester (II).

Reduction of the ester group in (II) with a dialkylaluminum hydride reagent, for example diisobutylaluminum hydride (one equivalent), at low temperature (−78° to −65° C.) in an inert solvent such as toluene followed by hydrolysis under neutral conditions gives the aldehyde (IV).

Reaction of freshly-distilled (IV) with a phosphorous ylid, for example, the sodium salt of 4-carboxybutyltriphenyl phosphorane (III) (E. J. Corey, et al., *J. Am. Chem. Soc.*, 91, 5675 (1969)] in dimethyl sulfoxide solution at 17°–25° C. results in the formation of the cis-olefin (V). The 2,5-dimethoxy-(or dialkoxy)-2,5-dihydrofuran group in (V) represents a latent enedione structure as indicated by the formation from it of linear compound (VI). The hydrolysis of (V) to (VI) may be effected with a weak acid, for example acetic acid or sodium dihydrogen phosphate, in a solvent system containing water and an organic cosolvent such as dioxane at a temperature of 25°–100° C. The linear enedione (VI) may be isolated or more conveniently subjected to further reaction in the hydrolysis system to induce the cyclization reaction which affords hydroxycyclopentenone (VIII).

With proper choice of conditions, for example operation in the pH range of 5.0 to 6.5 in the above temperature range, the dihydrofuran (V) directly affords the hydroxycyclopentenone (VIII). The product (VIII) may be isolated for the next step or used in situ in the rearrangement which leads to prostaglandin precursor (VII). In the latter case the hydrolysissolution, as defined above, is acidified with a strong acid, for example sulfuric acid, and the rearrangement of (VIII) to (VII) is allowed to occur at a temperature of 25°–100°-C., preferably about 65° C. for several hours. When the reaction is complete, as evidenced by the nearly total consumption of (VIII), the solution is extracted and the product (VII) is purified according to well-known procedures.

In the case where intermediate (VIII) is isolated, the rearrangement to (VII) may be carried out in a solution of strong acid as indicated above or in a solution of a weak base, for example sodium carbonate, in aqueous solution. For this reaction the best conditions are pH in the range 10.0–10.5 at about room temperature. The product (VII) is isolated and purified as above after acidication of the reaction solution.

The hydroxycyclopentenone (VII) represents a useful intermediate for the synthesis of prostaglandin $E_2$ (XII). For this purpose the hydroxy groups of (VII) are protected, for example by reaction with dihydropyran in the presence of an acid catalyst to give the bis-tetrahydropyranyl derivative (IX). Alternatively, hydroxy acid (VII) may be esterified, for example with ethereal diazomethane, to provide methyl ester (X). The remaining hydroxy group in X is protected as the tetrahydropyranyl ether to give (XI). The transformation of (IX) and (XI) to prostaglandin $E_2$, as well as the conversion of (XI) as the 4R enantiomer, has been reported by J. B. Heather et al., *Tetrahedron Letters*, 2313, (1973).

The cyclic acetal (V) is also a useful precursor to prostaglandins of the 11-deoxy class. When (V) is subjected to hydrolysis, as described above, in the presence of titanium trichloride, the linear enedione formed in the hydrolysis is reduced instead of cyclized to give ketoaldehyde (XIII). This conversion of (V) to (XIII) may be effected with a weak acid, for example acetic acid in the presence of sodium acetate, in a solvent system containing water and an organic cosolvent, such as dioxane, at 0°–50° C. and in the presence of at least two molar equivalents of titanium trichloride.

The ketoaldehyde (XIII) thus produced is converted to cyclopentenone (XV) by aldol cyclization with catalysis by a basic reagent, for example sodium hydroxide in aqueous solution. Cyclopentenone (XV) has been used as in intermediate for the synthesis of 11-deoxyprostaglandin $E_2$ (XIV) [P. A. Grieco and J. J. Reap, *J. Org. Chem.*, 38, 3413 (1973)].

For preparation of cyclopentenone (XX), a useful intermediate for the preparation of prostaglandin $E_1$ (XXII) [K. F. Bernady and M. J. Weiss, *Prostaglandins*, 3, 505 (1973)], a suitable starting material is 8-(2-furyl)-8-oxooctanoic acid (XVI) [R. I. Reed and W. K. Reid, *J. Chem. Soc.*, 1963, 5933]. Transformation of (XVI) to 8-(2-furyl)octanoic acid (XVII) is accomplished by Wolf-Kishner reduction which utilizes hydrazine and a solution of sodium hydroxide. The carboxyalkylfuran (XVII) is subjected to oxidative alkoxylation by procedures analogous to those used for preparation of the precursor to prostaglandin $E_2$, for example with bromine in a lower alkanol (e.g., methanol) in the presence of sodium carbonate, to provide the 2,5-dimethoxy(or dialkoxy)-2,5-dihydrofuran derivative (XVIII). The sequence of reactions leading to the useful compound (XX) from (XVIII) is carried out essentially as described above for the preparation of (IX) from (V). As before, intermediates (XIX) and (XXI) may be isolated or preferably used in situ as in the case of (VI) and (VIII).

The cyclic acetal (XVIII) is also a useful intermediate for the preparation of 11-deoxyprostaglandin $E_1$. Reaction of (XVIII) with a weak acid in the presence of titanium trichloride, as described above for the conversion of (V) to (XIII), affords ketoaldehyde (XXIII). Conversion of (XXIII) to (XXV) is effected with aqueous sodium hydroxide, as described above for the conversion of (XIII) to (XV). The carboxy group in (XXV) is protected by esterification, for example by treatment with ethanol in the presence of an acid catalyst to provide the ethyl ester (XXIV). Cyclopentenone (XXIV) has been used as an intermediate for the preparation of 11-deoxyprostaglandin $E_1$ (XXVI) [M. B. Floyd and M. J. Weiss, *Prostaglandins*, 3, 921 (1973)].

Adaptation of the above-described procedures to the preparation of the other compounds of this invention essentially involves the lengthening or shortening of, or the introduction of one or two lower alkyl groups into, the side-chains in furans (I) or (XVII) or in phosphonium derivative (III). These adaptations can be accomplished by procedures well-known to the art. For example, isopropyl γ-(2-furyl)-butyrate provides 2,5-dihydro-2,5-di-n-propoxy-2-(3'-carboisopropoxypropyl)furan in n-propanol whereas methyl δ-(2-furyl)valerate provides 2,5-dihydro-2,5-diethoxy-2-(4'-carbomethoxybutyl)furan in ethanol when treated in the manner described for the conversion of (I) to (II). Similarly, ω-(2-furyl)caproic acid and ω-(2-furyl)enanthic acid provide 2,5-dihydro-2,5-diethoxy-2-(5'-carboxyentyl)furan and 2,5-dihydro-2,5-diethoxy-2-(6'-carboxyhexyl)furan when treated in ethanol in the manner described for the conversion of (XVII) to (XVIII). Optionally, the furyl acids may be first esterified prior to oxidative alkoxylation, and all 2,5-dihydro-2,5-dialkoxy-2-(carboalkoxyalkyl)furans may be converted to the corresponding aldehydes in the manner described for the conversion of (II) to (IV). Also, the reaction of 3-carboxypropyltriphenylphosphonium bromide and 5-carboxy-3,4-dimethylamyltriphenylphosphonium bromide with 2,5-dihydro-2,5-diethoxy-2-(4'-oxobutyl)furan and 2,5-dihydro-2,5-diethoxy-2-(2'-oxoethyl)furan, respectively, provides the 2,5-dihydro-2,5-diethoxy-2-(7'-carboxy-4'-cis-heptenyl)furan and 2,5-dihydro-2,5-diethoxy-2-(7'-carboxy-5',6'-dimethyl-2-cis-heptenyl)furan.

Certain of the resulting 4-hydroxycyclopentenones and 4-unsubstituted cyclopentenones as well as their conversion to useful prostaglandin types are described in Netherlands patent specifications 7310–276 and 7310–277, both issued Jan. 28, 1974 (see *Derwent Central Patents Index*, Basic Abstracts Journal, B-Farmdoc, 10735 V/06 and 10736 V/06, respectively). Other useful prostaglandins with one or two lower alkyl substituents in the 2 or 3 positions, are described in U.S. Pat. No. 3,767,695 (Oct. 23, 1973).

The invention will be described in greater detail in conjunction with the following specific examples.

EXAMPLE 1

Preparation of 2,5-dihydro-2,5-dimethoxy-2-(2'-carbethoxyethyl)furan

To a stirred solution of 2-(2'-carbethoxyethyl)furan (42.5 g.) in 750 ml. of methanol containing 53 g. of sodium carbonate at −25° C. is added a solution of 40.5 g. of bromine in 250 ml. of methanol during the course of 2.5 hours. The solution is stirred at room temperature for 30 minutes, diluted with brine, and extracted with diethyl ether. The extract is washed with brine, dried over magnesium sulfate, and concentrated. The residue is distilled to provide a light yellow liquid, b.p. 78°–84° C. (0.2 mm.), $\nu$ max 1740 (ester carbonyl group) and 1015 cm$^{-1}$ (dimethoxydihydrofuran group).

EXAMPLE 2

Preparation of 2,5-dihydro-2,5-dimethoxy-2-(3'-oxopropyl)furan

To a stirred solution of 48.9 g. of 2,5-dihydro-2,5-dimethoxy-2-(2'-carbethoxyethyl)furan (Example 1) in 800 ml. of toluene was added 263 ml. of 0.89M diisobutylaluminum hydride in toluene during 90 minutes at −75° C. The solution was stirred at −75° C. for 30 minutes and then treated with 5.0 ml. of methanol. The stirred solution is treated with 100 ml. of water, and the resulting mixture is stirred at 0°–5° C. for 15 minutes, saturated with sodium sulfate, and filtered through Celite with the aid of ethyl acetate. The filtrate is washed with brine, dried over magnesium sulfate, and concentrated. The residue is distilled to provide a light yellow liquid, b.p. 76°–78° C. (0.25 mm.), $\nu$ max 1725 (aldehyde carbonyl group) and 1015 cm$^{-1}$ (dimethoxydihydrofuran group).

EXAMPLE 3

Preparation of 2,5-dihydro-2,5-dimethoxy-2-(7'-carboxy-3'-cis-heptenyl)furan

A solution of 35.8 g. of 2,5-dihydro-2,5-dimethoxy-2-(3'-oxopropyl)furan (Example 2) in 150 ml. of dimethylsulfoxide was added during 20 minutes at 17°–20° C. to a stirred solution of the Wittig reagent [(E. J. Corey, et al., *J. Am. Chem. Soc.*, 91, 5675 (1969)] prepared from 18.5 g. of 57% sodium hydride dispersion, 98 g. of 4-carboxybutyltriphenylphosphonium bromide, and 590 ml. of dimethylsulfoxide. The Jeep red solution was stirred at ambient temperature for 60 minutes, and then the dimethylsulfoxide was distilled from the mixture in a bath at 55° C. in vacuo. The resulting sludge is partitioned between water and ethyl acetate. The aqueous phase is acidified to pH 6.0, saturated with sodium chloride, and extracted with 3:2 diethyl ether:petroleum ether. The extract is washed with brine, dried over magnesium sulfate, and concentrated to give an oil, $\nu$ max 1700 (carboxylic acid group) and 1015 cm$^{-1}$ (dimethoxydihydrofuran group).

EXAMPLE 4

Preparation of 9,12-dioxo-5-cis-dodecenoic acid

To a stirred solution of 4.92 g. of sodium acetate in 40 ml. of water was added a solution of 2.70 g. of 2,5-dihydro-2,5-dimethoxy-2-(7'-carboxy-3'-cis-heptenyl)furan (Example 3) in 50 ml. of 2:2 dioxane:water. The resulting stirred solution was treated during 5 minutes with 15.6 ml. of 1.6M aqueous titanium trichloride at 25° C. The dark mixture was stirred for 30 minutes, diluted with brine and ethyl acetate, and filtered through Celite. The aqueous phase of the filtrate is extracted with ethyl acetate. The combined organic phases are washed with brine, dried over magnesium sulfate, and concentrated to give an oil, pmr (CDCl$_3$) 2.75 (—CH$_2$CH$_2$— group) and 9.86 $\delta$ (aldehyde group).

EXAMPLE 5

Preparation of 2-(6'-carboxy-2'-cis-hexenyl)cyclopent-2-en-1-one

A solution of 226 mg. of 9,12-dioxo-5-cis-dodecenoic acid (Example 4) in 10 ml. of 0.60N sodium hydroxide was allowed to stand at room temperature for 60 minutes. The solution was acidified with 4N HCl, saturated with sodium chloride and extracted with ethyl acetate. The extract is washed with brine, dried over magnesium sulfate, and concentrated. The residue is purified by chromatography on silica gel to give an oil, pmr (CDCl$_3$) 2.95 (1'-hydrogen atoms) and 7.35 $\delta$ (3-hydrogen atom).

EXAMPLE 6

Preparation of 2-(6'-carboxy-2'-cis-hexenyl)-3-hydroxycyclopent-4-en-1-one

To a stirred solution of 6.90 g. of sodium dihydrogen phosphate monohydrate and 3.55 g. of disodium hydrogen phosphate in 125 ml. of water and 115 ml. of 3:2 dioxane:water was added a solution of 6.76 g. of 2,5-dihydro-2,5-dimethoxy-2-(7'-carboxy-3'-cis-heptenyl)furan (Example 3) in 10 ml. of 3:2 dioxane: water. The resulting solution, pH 6.2, containing 9,12-dioxo-5cis,10-cis-dodecadienoic acid is heated at 45° C. for 45 hours. The course of the reaction is observed by workup as below of small aliquots and examination by thin layer chromatography and pmr. The reaction solution is worked up when the intermediate 9,12-dioxo-5-cis,10-cis-dodecadienoic acid (Example 10) is completely consumed. The solution is poured into 250 ml. of brine containing 7.5 ml. of 4N HCl and extracted with ethyl acetate. The extract is washed with brine, dried over magnesium sulfate, and concentrated. The residue is purified by column chromatography on silica gel to provide an oil, $\nu$ max 3370 (hydroxy group), 1710 (carbonyl groups), and 1595 cm$^{-1}$ (conjugated olefin group); pmr (CDCl$_3$) 4.70 (carbinolic hydrogen atom) and 7.53 $\delta$ (4-hydrogen atom).

EXAMPLE 7

Preparation of 2-(6'-carboxy-2'-cis-hexenyl)-4-hydroxycyclopent-2-en-1-one

A solution of 2.00 g. of 2-(6'-carboxy-2'-cis-hexenyl)-3-hydroxycyclopent-4-en-1-one (Example 6) and 3.77 g. of sodium carbonate in 89 ml. of water is allowed to stand at room temperature for 24 hours. The solution is acidified with 4N HCl, saturated with sodium chloride, and extracted with ethyl acetate. The extract is washed with brine, dried over magnesium sulfate, and concentrated to give an oil, pmr (CDCl$_3$) 4.95 (carbinolic hydrogen atom) and 7.19 $\delta$ (3-hydrogen atom).

EXAMPLE 8

Preparation of 4-carboxy-2-methylbutyltriphenylphosphonium bromide

A stirred solution of 61.3 g. of (R)-5-bromo-4-methylpentanoic acid [J. S. Dalby et al., *J. Chem. Soc.*, 1962, 4387], 92.0 g. of triphenylphosphine, and 160 ml. of acetonitrile is refluxed for 96 hours. The solution is cooled until crystallization begins and then diluted with 750 ml. of diethyl ether to complete the precipitation. The salt is obtained by filtration and is dried in vacuo at 75° C., m.p. 151°–165° C.

EXAMPLE 9

Preparation of 2-(6'-carboxy-4'-methyl-2'-cis-hexenyl)-4-hydroxycyclopent-2-en-1-one A solution of 5.01 g. of 2,5-dihydro-2,5-dimethoxy-2-(3'-oxopropyl)furan (Example 2) in 10 ml. of dimethylsulfoxide is added during 10 minutes at 18°–20° l C. to a stirred solution of the Wittig reagent prepared from 2.57 g. of 57% sodium hydride dispersion, 14.1 g. of 4-carboxy-2-methylbutyltriphenylphosphonium bromide (Example 8), and 90 ml. of dimethylsulfoxide. The deep red solution is stirred at room temperature for 16 hours and then the dimethylsulfoxide is distilled from the mixture in vacuo from a bath at 65° C. The resulting sludge is stirred with water at 0° C. for 30 minutes, and the resulting insoluble triphenylphosphine oxide is removed by filtration.

The aqueous filtrate containing 2,5-dihydro-2,5-dimethoxy-2-(7'-carboxy-5'-methyl-3-cis-heptenyl)furan is treated with 23.9 g. of sodium dihydrogen phosphate monohydrate, the mixture is diluted with 80 ml. of dioxane, and the resulting solution containing 9,12-dioxo-4-methyl-5-cis,10-cis-dodecadienoic acid is heated at 45° C. for 66 hours. The stirred solution is treated during 5 minutes with 21 ml. of concentrated sulfuric acid and this solution is heated at 65° C. for 16 hours. The solution is cooled, saturated with sodium chloride, and extracted with ethyl acetate. The extract is washed with brine and extracted with sodium bicarbonate solution. The aqueous extract is acidified with 4N hydrochloric acid, saturated with sodium chloride, and extracted with ethyl acetate. This extract is washed with brine, dried over magnesium sulfate, and concentrated. The residue is purified by column chromatography on silica gel to provide an oil, $\nu$ max 3370 (hydroxy group), 1710 (carbonyl groups), and 1595 cm$^{-1}$ (conjugated olefin group); pmr (CDCl$_3$) 0.96 (doublet, methyl group), 4.95 (carbinolic hydrogen atom), and 7.19 $\delta$ (3-hydrogen atom).

EXAMPLE 10

Preparation of 9,12-dioxo-5-cis,10-cis-dodecadienoic acid

A stirred solution of 1.35 g. (5.0 mmoles) of 2,5-dihydro-2,5-dimethoxy-2-(7'-carboxy-3'-cis-heptenyl)furan (Example 3) in 25 ml. of tetrahydrofuran:water (85:15) is heated to 45° C. during 15 minutes. To the solution is added 0.60 g. of acetic acid and this solution is heated at 45° C. for 24 hours. The solution is diluted with brine and extracted with diethyl ether. The extract is washed with brine, dried over magnesium sulfate, and concentrated to give an oil.

Separation of the product is accomplished by thin layer chromatography on silica gel with heptane:ethyl acetate:acetic acid (60:40:2) to give an oil, pmr (CDCl$_3$) 10.2 $\delta$ (doublet, J=7 cps, aldehyde group). The compound gives a characteristic green spot, R$f$ = 0.29, when developed with the above chromatography system and sprayed with 2,4-dinitrophenylhydrazine reagent.

Also obtained from the reaction and chromatography is the 5-cis,10-trans isomer, pmr (CDCl$_3$) 9.82 $\delta$ (quartet, J=2 and 6 cps, aldehyde group). The compound gives a characteristic orange spot, R$f$ = 0.34, when developed with the above chromatography system and sprayed with 2,4-dinitrophenylhydrazine reagent.

1. A compound of the formula:

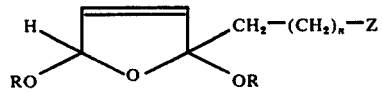

wherein $n$ is selected from the group consisting of zero and an integer from 1 to 2; R is alkyl having up to 3 carbon atoms; and Z is formyl.

2. The compound according to claim 1 wherein n is 1, R is methyl, and Z is formyl; 2,5-dihydro-2,5-dimethoxy-2-(3'-oxopropyl)furan.

3. A compound of the formula:

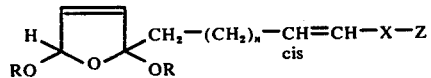

wherein $n$ is selected from the group consisting of 0, 1 and 2; R is alkyl having up to 3 carbon atoms; X is a divalent straight chain alkylene group having from 2 to 4 carbon atoms and optionally substituted with 1 to 2 methyl groups; and Z is selected from the group consisting of carboxy and carboalkoxy having up to 4 carbon atoms.

4. The compound according to claim 3 wherein $n$ is 1, R is methyl, X is —CH$_2$CH$_2$CH$_2$—, and Z is carboxy; 2,5-dihydro-2,5-dimethoxy-2-(7'-carboxy-3'-cis-heptenyl)furan.

5. The compound according to claim 3 wherein $n$ is 1, R is methyl, X is —CH(CH$_3$)CH$_2$CH$_2$—, and Z is carboxy; 2,5-dihydro-2,5-dimethoxy-2-(7'-carboxy-5'-methyl-3'-cis-heptenyl)-furan.

* * * * *